(12) United States Patent  (10) Patent No.: US 7,544,797 B2
Seo et al.  (45) Date of Patent: Jun. 9, 2009

(54) PROCESSES FOR THE PREPARATION OF CEPHEM DERIVATIVES

(75) Inventors: Dae Won Seo, Gunpo (KR); In Hwa Chung, Yongin (KR); Ki Bong Lee, Cheongju (KR); In Kyu Lee, Gunpo (KR)

(73) Assignee: CJ Cheiljedang Corporation, Seoul (KR)

( * ) Notice: Subject to any disclaimer, the term of this patent is extended or adjusted under 35 U.S.C. 154(b) by 386 days.

(21) Appl. No.: 10/577,552

(22) PCT Filed: Oct. 30, 2004

(86) PCT No.: PCT/KR2004/002770

§ 371 (c)(1),
(2), (4) Date: Apr. 28, 2006

(87) PCT Pub. No.: WO2005/042543

PCT Pub. Date: May 12, 2005

(65) Prior Publication Data

US 2007/0060747 A1 Mar. 15, 2007

(30) Foreign Application Priority Data

Oct. 30, 2003 (KR) .................. 10-2003-0076354
Oct. 30, 2003 (KR) .................. 10-2003-0076357
Oct. 30, 2003 (KR) .................. 10-2003-0076358
Oct. 30, 2003 (KR) .................. 10-2003-0076359

(51) Int. Cl.
*C07D 501/22* (2006.01)
*C07D 501/36* (2006.01)
*C07F 9/54* (2006.01)

(52) U.S. Cl. ............... 540/215; 540/226; 540/230

(58) Field of Classification Search ............ 568/11; 540/226, 230, 215
See application file for complete search history.

(56) References Cited

U.S. PATENT DOCUMENTS

| 3,985,741 A | 10/1976 | Crast, Jr. et al. |
| 4,243,819 A | 1/1981 | Henrick et al. |
| 4,336,376 A | 6/1982 | Coll et al. |
| 4,464,307 A | 8/1984 | Baer et al. |
| 4,661,590 A | 4/1987 | Hoshi et al. |
| 4,708,825 A | 11/1987 | Ascher et al. |
| 4,727,070 A | 2/1988 | Kaplan et al. |

FOREIGN PATENT DOCUMENTS

| EP | 0503453 A2 | 9/1992 |
| FR | 2580652 A1 | 10/1986 |
| GB | 2 135 305 A | 8/1984 |
| GB | 2173798 A | 10/1986 |
| KR | 2002-0069431 A | 9/2002 |
| KR | 2002-0069432 A | 9/2002 |
| KR | 2002-0069437 A | 9/2002 |
| KR | 2002-0069440 A | 9/2002 |
| KR | 2002-0080838 A | 10/2002 |

*Primary Examiner*—Mark L Berch
(74) *Attorney, Agent, or Firm*—Rothwell, Figg, Ernst & Manbeck, P.C.

(57) ABSTRACT

Provided is a process for preparing a compound of formula 1 or its salt, which includes reacting a compound of formula 2 with a compound of formula 3 in the presence of a base.

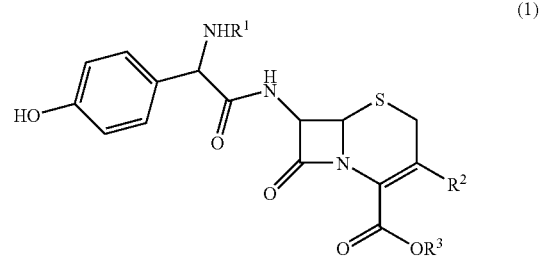

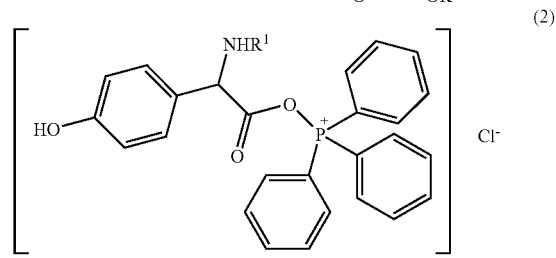

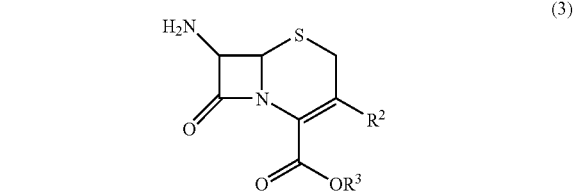

14 Claims, No Drawings

PROCESSES FOR THE PREPARATION OF CEPHEM DERIVATIVES

CROSS REFERENCE TO RELATED APPLICATION

This application is a 35 U.S.C. § 371 National Phase Entry Application from PCT/KR2004/002770, filed Oct. 30, 2004, and designating the U.S.

BACKGROUND OF THE INVENTION

1. Field of the Invention

The present invention relates to a process for preparing cephalosporin antibiotics, including cefprozil, cefatrizine, and cefadroxil, using a 4-hydroxyphenylglycine derivative.

2. Description of the Related Art

Oral cephalosporin antibiotics, including cefprozil, cefatrizine, and cefadroxil, commonly have a 4-hydroxyphenylglycine group, as represented by the following formula:

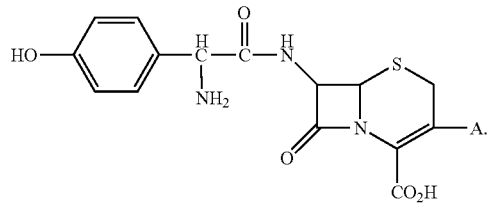

The compound of the above formula is cefprozil when A is —C═CH—CH$_3$, cefatrizine when A is 1H-1,2,3-triazole-4-yl-thiomethyl, and cefadroxil when A is —CH$_3$.

Conventionally, there have been known various processes for preparing oral cephalosporin antibiotics, such as cefprozil, cefatrizine, and cefadroxil, by reacting reactive derivatives of 4-hydroxyphenylglycine with 3-cephem compounds.

For example, U.S. Pat. No. 3,985,741 discloses a process for preparing a cefadroxil, which includes reacting 4-hydroxyphenylglycine and ethylchloroformate in N-methylmorpholine to obtain an anhydride, followed by reaction with 7-amino-deacetoxy-cephalosporanic acid (7-ADCA). However, the yield and quality of the product are poor.

U.S. Pat. Nos. 4,520,022, 4,591,641, and 4,661,590 disclose a condensation reaction between 4-hydroxyphenylglycine with a protected amino group and a cephem compound in the presence of N,N'-dicyclohexylcarbodimide. However, N,N'-dicyclohexylurea produced after the condensation reaction is not easily removed, which restricts industrial applications.

U.S. Pat. No. 4,336,376 discloses a process for preparing a cefadroxil, which includes reacting a 4-hydroxyphenylglycine salt having a protected amino group with trimethylsilyl-2-oxazolidinone to protect a 4-hydroxyl group followed by reaction with acylchloride to obtain a 4-hydroxyphenylglycine anhydride and then reaction with 7-ADCA. However, silylation is prerequisite and these reactions are annoying, and thus, this process is not suitable for industrial application.

U.S. Pat. No. 4,708,825 discloses a technique of reacting 4-hydroxyphenylglycine having a substituted amino group with thionyl chloride using a gaseous hydrogen chloride to obtain a 4-hydroxyphenylglycyl chloride hydrochloride followed by reaction with a cephem compound. However, handling property of the thionyl chloride and the gaseous hydrogen chloride is poor, and thus, this technique is not suitable for industrial application.

U.S. Pat. Nos. 3,925,418, 4,243,819, and 4,464,307 disclose a process for producing 4-hydroxyphenylglycine using excess phosgene. However, difficulty in handling of highly toxic phosgene, removal of excess residual phosgene, and control of reaction conditions renders mass production difficult.

As a process for preparing a reactive anhydride of 4-hydroxyphenylglycine, there are reported a method for the preparation of acid chloride using phosphorus pentachloride, phosphorus oxychloride, or thionyl chloride, and a method for the preparation of active ester using imidazole, mercaptobenzothiazole, or hydroxybenzotriazole. However, an acid chloride of 4-hydroxyphenylglycine has poor reactivity due to a hydroxyl group and an active ester of 4-hydroxyphenylglycine has poor reactivity and involves a side reaction.

In addition, Korean Patent Laid-Open Publication Nos. 2002-69431, 2002-69432, 2002-69437, and 2002-69440 disclose a process for preparing a pivaloyl or succinimide derivative of 4-hydroxyphenylglycine and a process for preparing a cephem compound such as cefprozil using the pivaloyl or succinimide derivative of 4-hydroxyphenylglycine.

Meanwhile, there have been known various preparation processes for 3-(Z)-propenyl cephem derivative which is a compound useful as an intermediate for preparation of cefprozil which is an oral cephalosporin antibiotic.

WO93/16084 discloses a process of selectively separating a 3-(Z)-propenyl cephem compound by means of a hydrochloride, metal, or tertiary amine salt of 7-amino-3-(1-propen-1-yl)-3-cephem-carboxylic acid or by adsorption chromatography. However, there is a disadvantage in that separation and purification are cost-ineffective.

U.K. Patent No. 2,135,305 discloses a process for preparing cefprozil from a 4-hydroxyphenylglycine compound with a t-butoxycarbonyl-protected amino group and a cephem compound with a benzhydryl-protected carboxyl group. However, incorporation of a 3-propenyl group after acylation lowers reaction efficiency and high-performance liquid chromatography is required for isomer separation, which render industrial application difficult.

U.S. Pat. No. 4,727,070 discloses a technique of removing an E-isomer cefprozil from a mixture of Z/E cefprozil, which includes incorporating an active group such as sodium imidazolidinone into the mixture of Z/E cefprozil by reaction of the mixture of Z/E cefprozil with acetone followed by deprotection. However, purification by chromatography incurs enormous costs.

In view of the above problems, Korean Patent Laid-Open Publication No. 2002-80838 discloses a process for preparing a 3-(Z)-propenyl cephem compound by reacting a phosphoranylidene cephem compound with acetaldehyde in a mixed solvent essentially consisting of ether in the presence of a base. According to a disclosure in this patent document, ether is essentially used. In this respect, in the case of using methylenechloride or tetrahydrofuran, even when other reaction conditions, for example, reaction temperature, reaction duration, base, catalyst, and the like are adjusted, it is very difficult to adjust the content of the Z-isomer to more than 83%.

SUMMARY OF THE INVENTION

The present invention provides a process for simply preparing a cephalosporin antibiotic in high yield and purity using a novel reactive intermediate, i.e., a 4-hydroxyphenylglycine derivative.

The present invention also provides a novel reactive intermediate, i.e., a 4-hydroxyphenylglycine derivative which is used in simply preparing a cephalosphorin antibiotic in high yield and purity, and a preparation process thereof.

While searching for a process for stereospecifically preparing a novel 3-(Z)-propenyl cephem derivative, the present inventors found that use of a mixed solvent including methylenechloride, isopropylalcohol, and water in a predetermined ratio can stereospecifically and efficiently produce the 3-(Z)-propenyl cephem derivative, which is in contrary to the disclosure in Korean Patent Laid-Open Publication No. 2002-80838.

Therefore, the present invention also provides a process for stereospecifically preparing a 3-(Z)-propenyl cephem derivative using a mixed solvent including methylenechloride, isopropylalcohol, and water in a predetermined ratio.

DETAILED DESCRIPTION OF THE INVENTION

According to an aspect of the present invention, there is provided a process for preparing a compound represented by the following formula 1 or its salt, which includes reacting a compound represented by the following formula 2 with a compound represented by the following formula 3 in the presence of a base:

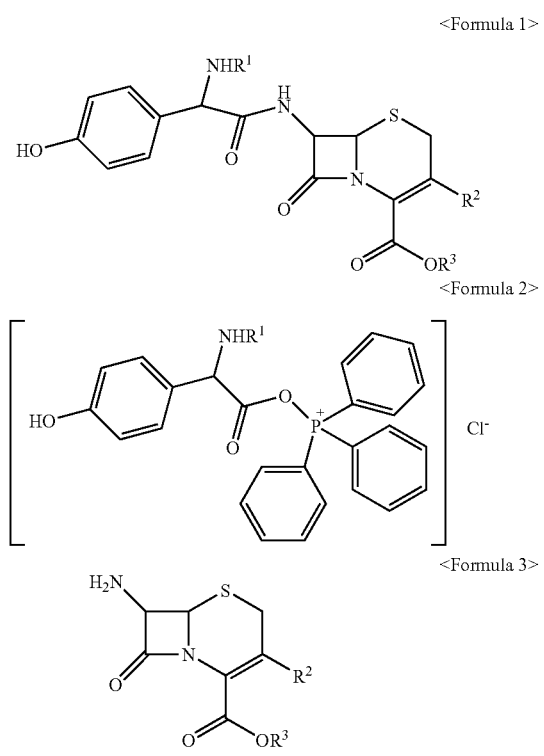

wherein $R^1$ is a hydrogen or an amino protecting group, $R^2$ is methyl, propen-1-yl, or 1H-1,2,3-triazole-4-yl-thiomethyl, and $R^3$ is a hydrogen or a carboxyl protecting group.

The salt of the compound of the formula 1 refers to a salt commonly known in the field of cephalosporin antibiotics, for example a hydrate or an acid addition salt.

The amino protecting group may be that commonly used in preparation of cephalosporin antibiotics. Examples of the amino protecting group include formyl, acetyl, benzyl, benzylidene, diphenylmethyl, triphenylmethyl, trichloroethoxycarbonyl, t-butoxycarbonyl, 2-methoxycarbonyl-1-methyl-vinyl, and 2-ethoxycarbonyl-1-methyl-vinyl. In the above compounds, it is preferred that $R^1$ is 2-ethoxycarbonyl-1-methyl-vinyl in terms of cost effectiveness, handling property, and yield of a final product. Incorporation of a 2-ethoxycarbonyl-1-methyl-vinyl group can be accomplished by use of ethyl acetoacetate.

The carboxyl protecting group may be that commonly used in preparation of cephalosporin antibiotics. Examples of the carboxyl protecting group include allyl, benzyl, p-methoxybenzyl, p-nitrobenzyl, triphenylmethyl, and diphenylmethyl.

In the preparation process of the present invention, it is preferred that the compound of the formula 2 is used as an anhydride form.

Preferably, the compound of the formula 2 reacts with the compound of the formula 3 at an equivalent ratio of 1-3 to 1, preferably 1.1-1.5 to 1. Preferably, the reaction of the compound of the formula 2 with the compound of the formula 3 is performed in a mixed solvent of water with an organic solvent selected from the group consisting of dimethylsulfoxide, dimethylformamide, dimethylacetamide, 1,4-dioxane, acetonitrile, dichloromethane, and a mixture thereof. More preferred are dimethylacetamide and dichloromethane as the organic solvent. Preferably, in the mixed solvent, water is used in an amount of 0.05 to 0.3 parts by weight, preferably 0.1 to 0.2 parts by weight, based on 1 part by weight of the organic solvent. The reaction of the compound of the formula 2 with the compound of the formula 3 is performed at a temperature of −50 to −20° C., preferably −40 to −30° C., for 1 to 4 hours, preferably 1.5 to 2.5 hours.

Examples of the base that can be used herein include N-methylmorpholine, triethylamine, diethylamine, n-tributylamine, N,N-dimethylaniline, and pyridine. Among them, triethylamine is preferable. Preferably, the base is used in an amount of 1 to 2 equivalents (eq.), and preferably 1.05 to 1.2 eq., based on 1 eq. of the compound of the formula 2.

The compound of the formula 2 may be obtained by reacting a compound represented by the following formula 4 with dichlorotriphenylphosphorane in the presence of a base:

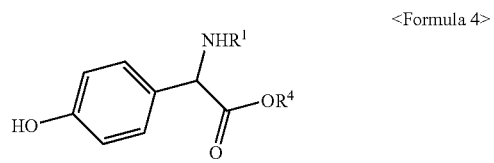

wherein $R^1$ is a hydrogen or an amino protecting group and $R^4$ is hydrogen, sodium, or potassium.

The compound of the formula 4 in which $R^1$ is an amino protecting group can be prepared as a compound with a desired amino protecting group by common amino protection of 4-hydroxyphenylglycine.

Preferably, dichlorotriphenylphosphorane reacts with the compound of the formula 4 at an equivalent ratio of 1-5 to 1, and preferably 1.1-1.5 to 1. The reaction of the compound of the formula 4 with dichlorotriphenylphosphorane may be performed in an organic solvent selected from the group consisting of dichloromethane, acetonitrile, and tetrahydrofuran. The reaction may be performed at a temperature of −30 to 20° C., preferably −5 to 5° C., for 1 to 5 hours, preferably 1 to 2 hours. Examples of the base that can be used in the reaction of the compound of the formula 4 with dichlorotriphenylphosphorane include triethylamine, diethylamine, n-tributylamine, N,N-dimethylaniline, and pyridine. Triethylamine is preferable. Preferably, the base is used in an amount of about 1 to 1.5 eq., and preferably 1.1 to 1.3 eq., based on 1 eq. of the compound of the formula 2.

Preferably, dichlorotriphenylphosphorane can be obtained by reaction of triphenylphosphine and hexachloroethane, as represented by the following reaction scheme 1:

<Reaction Scheme 1>

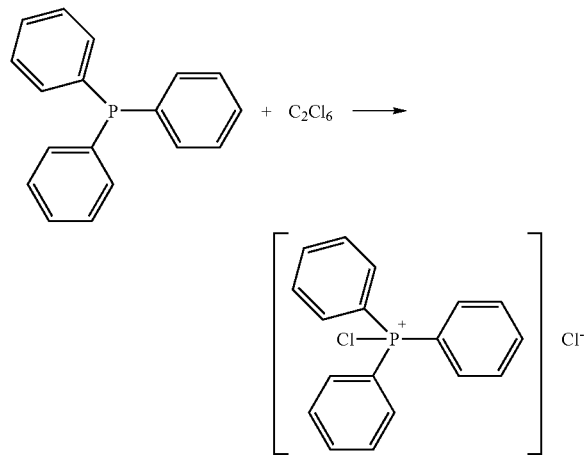

The reaction represented by the reaction scheme 1 may be performed in an organic solvent at about −5 to 5° C., and preferably about 0° C., for about 1 to 3 hours, and preferably about 2 hours. Examples of the organic solvent that can be used include tetrahydrofuran, dichloromethane, chloroform, carbon tetrachloride, dimethylformamide, dimethylacetamide, 1,4-dioxane, and acetonitrile. Preferred are dichloromethane and dimethylacetamide.

The compound of the formula 2 used as a reaction intermediate has good solubility in an organic solvent commonly used in synthesis of cephalosporin compounds, for example, methylenechloride or acetonitrile. Therefore, a solution containing the compound of the formula 2 can be directly used as a reaction solution for a next process (e.g., acylation) without a separate separation process such as filtration and drying, whereby an entire process can be performed by one-pot reaction.

In this respect, it is preferred that the reaction of triphenylphosphine and hexachloroethane, the reaction of the compound of the formula 4 and dichlorotriphenylphosphorane in the presence of a base, and the reaction of the compound of the formula 2 and the compound of the formula 3 in the presence of a base are performed by one-pot reaction without a separate separation process, which is as represented by the following reaction scheme 2.

<Reaction Scheme 2>

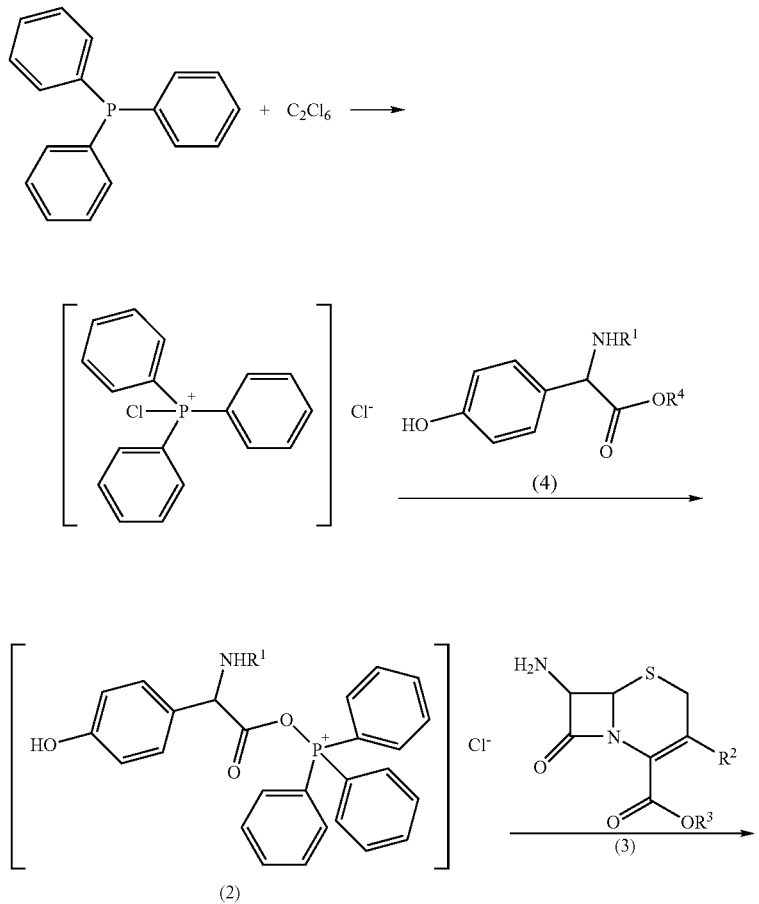

-continued

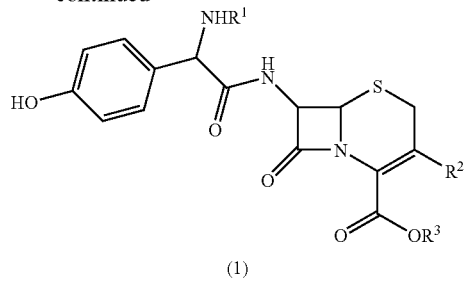

(1)

According to another aspect of the present invention, there is provided a compound useful as an intermediate for preparation of a cephalosporin compound with a 4-hydroxyphenylglycine group, such as cefaprozil, cefadroxil, and cefatrizine. That is, the present invention also provides a compound of the following formula 2:

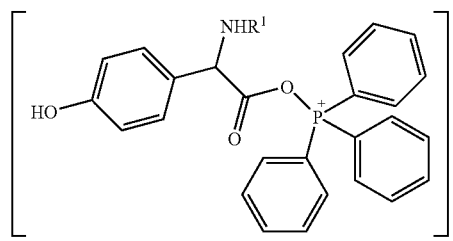

<Formula 2> wherein $R^1$ is a hydrogen or an amino protecting group.

Preferably, the compound of the formula 2 is an anhydride form. An anhydride form of the compound of the formula 2 can be efficiently used in preparation of cephalosporin antibiotics.

The amino protecting group may be that commonly used in preparation of cephalosporin antibiotics, for example including formyl, acetyl, benzyl, benzylidene, diphenylmethyl, triphenylmethyl, trichloroethoxycarbonyl, t-butoxycarbonyl, 2-methoxycarbonyl-1-methyl-vinyl, and 2-ethoxycarbonyl-1-methyl-vinyl. More preferable is a compound of formula 2 in which R1 is 2-ethoxycarbonyl-1-methyl-vinyl in terms of cost effectiveness, handling property, and yield of a final product. Incorporation of 2-ethoxycarbonyl-1-methyl-vinyl can be accomplished by use of ethyl acetoacetate.

The compound of the formula 2 has good solubility in an organic solvent commonly used in synthesis of cephalosporin compounds, for example, methylenechloride or acetonitrile. Therefore, a solution containing the compound of the formula 2 can be directly used as a reaction solution for a next process (e.g., acylation) without a separate separation process such as filtration and drying According to still another aspect of the present invention, there is provided a process for preparing a compound of the following formula 2, and more particularly, a process for preparing the compound of the formula 2, which includes reacting a compound of the following formula 4 with dichlorotriphenylphosphorane in the presence of a base:

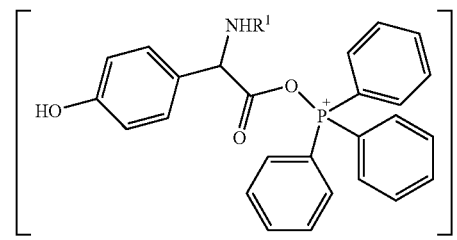

<Formula 2>

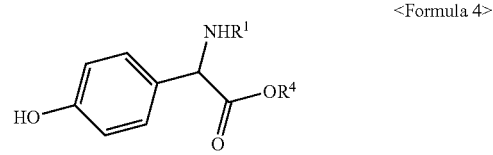

<Formula 4> wherein $R^1$ is a hydrogen or an amino protecting group and $R^4$ is hydrogen, sodium, or potassium.

The compound of the formula 4 in which R1 is an amino protecting group can be prepared as a compound with a desired amino protecting group (for example, the above mentioned amino protecting group) by common amino protection of 4-hydroxyphenylglycine.

According to the preparation process of the present invention, it is preferred that dichlorotriphenylphosphorane reacts with the compound of the formula 4 at an equivalent ratio of 1-5 to 1, preferably 1.1-1.5 to 1. Preferably, the reaction of the compound of the formula 4 with dichlorotriphenylphosphorane is performed in an organic solvent selected from the group consisting of dichloromethane, acetonitrile, tetrahydrofuran, and a mixture thereof, at a temperature of −30 to 20° C., and preferably −5 to 5° C., for 1 to 5 hours, and preferably 1 to 2 hours.

Examples of the base that can be used in the reaction of the compound of the formula 4 with dichlorotriphenylphosphorane include triethylamine, diethylamine, n-tributylamine, N,N-dimethylaniline, and pyridine. Among them, triethylamine is preferred. The base is used in an amount of about 1 to 1.5 eq., and preferably 1.1 to 1.3 eq., based on 1 eq. of the compound of the formula 4.

Dichlorotriphenylphosphorane can be obtained by reaction of triphenylphosphine and hexachloroethane, as represented by the following reaction scheme 1:

<Reaction Scheme 1>

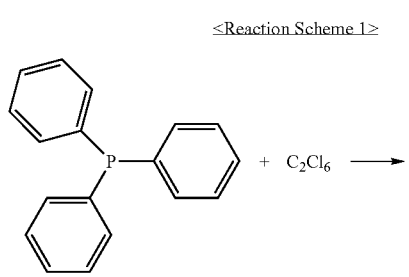

+ C₂Cl₆ ⟶

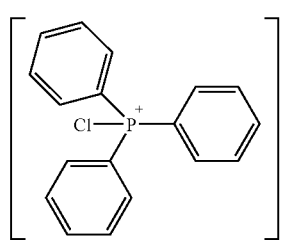

The reaction represented by the reaction scheme 1 can be performed in an organic solvent at about −5 to 5° C., and preferably about 0° C., for about 1 to 3 hours, and preferably about 2 hours. Examples of the organic solvent that can be used include tetrahydrofuran, dichloromethane, chloroform, carbon tetrachloride, dimethylformamide, dimethylacetamide, 1,4-dioxane, and acetonitrile. Preferred are dichloromethane and dimethylacetamide.

Preferably, the reaction of triphenylphosphine and hexachloroethane and the reaction of the compound of the formula 4 and dichlorotriphenylphosphrane in the presence of a base are performed by one-pot reaction without a separate separation process, as represented by the following reaction scheme 2a:

<Reaction Scheme 2a>

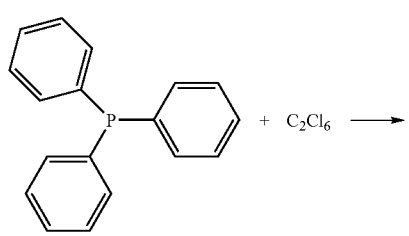

+ C₂Cl₆ ⟶

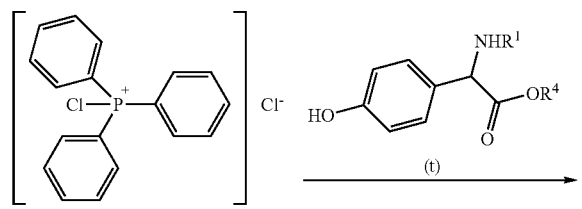

—(t)→

-continued

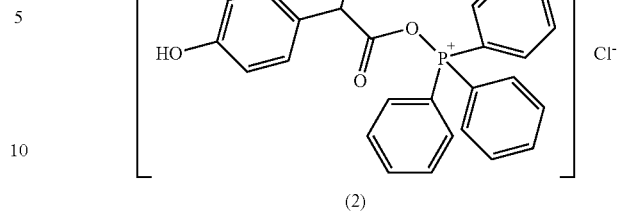

(2)

According to a further aspect of the present invention, there is provided a process for stereospecifically preparing a compound represented by the following formula 3a, which includes reacting a compound represented by the following formula 5 with acetaldehyde in a mixed solvent including water, isopropanol, and methylenechloride in a volume ratio of 1:3-6:11-14 in the presence of a base:

<Formula 3a>

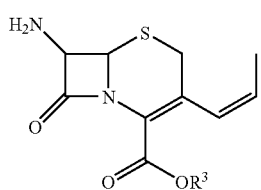

<Formula 5>

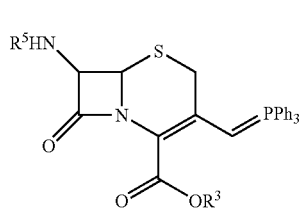

wherein $R^3$ is a hydrogen or a carboxyl protecting group, and $R^5$ is a hydrogen or an amino protecting group. The compound of the formula 3a thus prepared can be used as the compound of the formula 3 in the preparation of the compound of the formula 1.

As used herein, the term "stereospecific compound" refers to a mixed compound (e.g., the compound of the formula 1 or 4) composed of a Z-isomer (or cis-isomer) and an E-isomer (or a trans-isomer) in a ratio of about 89-94% to about 6-11%, i.e., a compound composed of a Z-isomer and an E-isomer in a ratio of about 8.1-15.7:1.0. In this respect, the term "stereospecific preparation process" refers to a process for preparing the "sterespecific compound".

The carboxyl protecting group and the amino protecting group may be protecting groups commonly used in synthesis of cephalosporin antibiotics. Examples of the carboxyl protecting group include allyl, benzyl, p-methoxybenzyl, p-nitrobenzyl, triphenylmethyl, and diphenylmethyl, and examples of the amino protecting group include benzylcarbonyl, 4-methoxybenzyl, benzylidene, diphenylmethyl, and triphenylmethyl. Preferably, the carboxyl protecting group and the amino protecting group are respectively 4-methoxybenzyl and benzylcarbonyl which are commercially available.

According to the preparation process of the present invention, when the reaction is performed in the mixed solvent including water, isopropanol, and methylenechloride in a volume ratio of 1:3-6:11-14, the compound of the formula 3a can be prepared stereospecifically, i.e., so that a Z-isomer and an E-isomer of the compound of the formula 3a are in a ratio of about 8.1-15.7:1.0, in high yield and purity, which can be seen from Table 1 of the following Examples. In particular, when the volume ratio of water, isopropanol, and methylenechloride in the mixed solvent is 1:4:12, the Z/E isomers with high ratio of Z/E can be obtained in high yield.

In preparation of the compound of the formula 3a, the mixed solvent may be used in an amount of about 5-20 times by weight, and preferably about 10-15 times by weight, based on the compound of the formula 5.

In preparation of the compound of the formula 3a, acetaldehyde may be used in an amount of about 5-30 eq., and preferably about 10 to 15 eq., based on 1 eq. of the compound of the formula 5. The preparation of the compound of the formula 3a may be performed at a temperature of about −20 to −10° C. for about 2 to 20 hours, preferably about 10 to 15 hours.

The compound of the formula 5 can be prepared according to a known method (e.g., Korean Patent Laid-Open Publication No. 2002-80838). That is, the compound of the formula 5 can be prepared by reacting a 3-halomethyl cephem compound represented by the following formula 6 with triphenylphosphine to obtain a phosphonium salt, followed by treatment with a base such as sodium hydroxide or sodium carbonate:

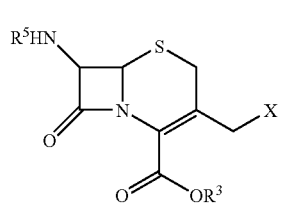

<Formula 6> wherein $R^3$ and $R^5$ are as defined in the above and X is halogen.

The preparation of the compound of the formula 5 and the preparation of the compound of the formula 3a can be performed by one-pot reaction without separately separating the compound of the formula 5. In this case, since the base used in the preparation of the compound of the formula 5 remains in a reaction solution, there is no need to further add a base in the preparation of the compound of the formula 3a, which simplifies preparation processes.

The compound of the formula 3a can be converted to 7-amino-3-[propen-1-yl]-3-cephem-4-carboxylic acid represented by the following formula 7 by common deprotection. The compound of the formula 7 can be efficiently used as an intermediate for preparation of cefprozil:

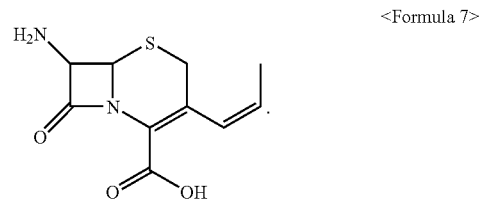

<Formula 7>

The compound of the formula 3a thus prepared can be used as the compound of the formula 3 in the preparation of the compound of the formula 1. In this case, the entire preparation process for a compound of the following formula 1a in which $R^2$ of the formula 1 is propen-1-yl can be represented by the following reaction scheme 2b:

<Reaction Scheme 2b>

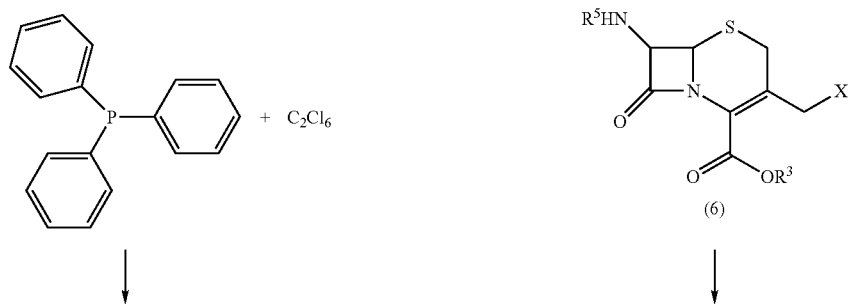

(6)

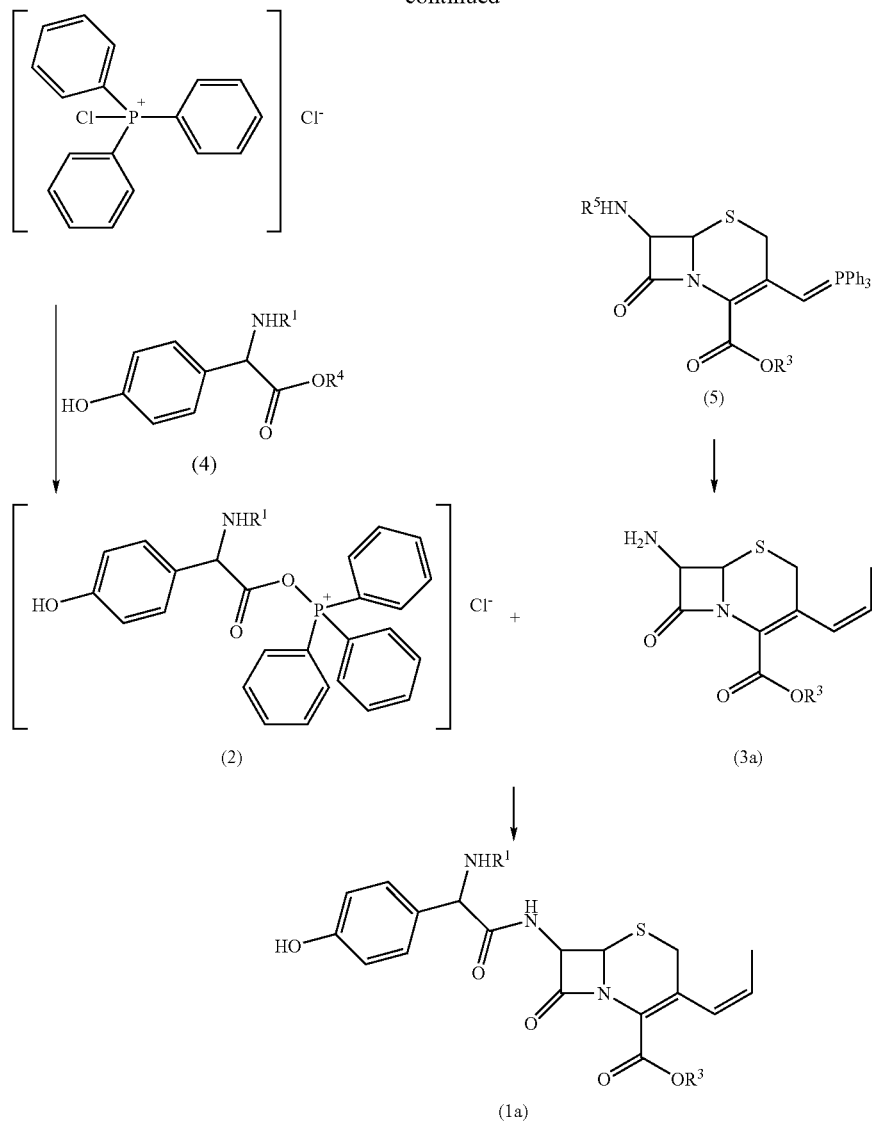

Hereinafter, the present invention will be described more specifically by Examples. However, the following Examples are provided only for illustrations and thus the present invention is not limited to or by them.

EXAMPLE 1

Preparation of (2-ethoxycarbonyl-1-methyl-vinylamino)-(4-hydroxyphenyl)-acyloxyphosphonium chloride Step A 9.9 g (0.038 mol) of triphenylphosphine and 8.8 g (0.038 mol) of hexachloroethane were sequentially added to 100 ml of methylenechloride. The reaction mixture was incubated at 0° C. for 2 hours and cooled to −5° C. 10 g (0.031 mol) of potassium (2-ethoxycarbonyl-1-methyl-vinylamino)-(4-hydroxyphenyl)-acetate and 8 g of triethylamine were sequentially added thereto and stirred for 2 hours.

Step B

A crystal precipitated in step A was filtered and washed with 20 ml of methylenechloride. An obtained filtrate was distilled under reduced pressure to remove a solvent. An obtained crystal was filtered and dried in vacuum to give 17.5 g (96.7%) of the titled compound as a white solid.

H-NMR($\delta$, CHCl$_3$-d$_1$) 1.31(3H, d, 8.6 Hz, —OCH$_2$CH$_3$), 1.75(1H, m, —NHC$\underline{H}$CHCO—), 4.23(2H, m, —OC$\underline{H_2}$CH$_3$), 4.51(1H, d, 8.3 Hz, —NHCHC$\underline{H}$CO—), 4.81(1H, $\overline{\text{d, 8.0 Hz}}$, —NHC$\underline{H}$(Ph)CO—), 6.63(2H, d, 8.0 Hz), 6.91(2H, d, 8.1 Hz), 7.31(6H, m), 7.65(9H, m)

EXAMPLE 2

Preparation of 7-phenylacetamido-3-[propen-1-yl]-3-cephem-4-carboxylic acid p-methoxybenzyl ester 16 g of sodium iodide and 28 g of triphenylphosphine were placed in a reactor containing 50 g (102.7 mmol) of 3-chloromethyl-7-phenylacetamido-3-[propen-1-yl]-3-cephem-4- carboxylic acid p-methoxybenzyl ester. 400 ml of methylenechloride was added thereto and stirred at 20° C. for 2 hours. After phase separation, 200 ml of a 20% sodium hydroxide was dropwise added to an obtained organic layer and stirred at 10° C. for 30 minutes. After separation of an organic layer, a phosphoranylidene solution was obtained.

200 ml of methylenechloride, 200 ml of isopropanol, and 50 ml of water were added to the phosphoranylidene solution and cooled to −20° C. 100 ml of acetaldehyde was dropwise added thereto and stirred for 20 hours. A 30% potassium thiosulfuric acid was dropwise added thereto and stirred for 30 minutes to separate an organic layer. The organic layer thus obtained was subjected to addition of 200 ml of isopropanol, concentrated to obtain a crystal, cooled to 0° C., and stirred for 2 hours to precipitate a solid. The solid was filtered and dried in vacuum to give 42.3 g (88.4 mmol, yield 86%, Z/E=10.111) of the titled compound as a white solid.

H-NMR($\delta$, DMSO-$d_6$): 1.52(3H×10.1/11.1, d, (Z)-$CH_3$), 1.73(3H×1.0/11.1, (E)-$CH_3$), 3.36-3.68(4H, m, ph$CH_2$, C-2), 3.75(3H, S, —$OCH_3$), 5.06-5.24(3H, m, $CO_2$—$CH_2$, C-6), 5.52-5.69(2H, d, —$CH$=CH($CH_3$), 6.06(1H, d, —CH=$CH$($CH_3$), C-7), 6.91(2H, d, ph), 7.19-7.62(7.19-7.62(7H, m, ph)

EXAMPLES 3 AND 4

7-phenylacetamido-3-[propen-1-yl]-3-cephem-4-carboxylic acid p-methoxy-benzyl ester was prepared in the same manner as in Example 2 except that the volume ratio of methylenechloride, isopropanol, and water was as listed in Table 1 below. The yields and Z/E isomer ratios of the compounds of Examples 2, 3, and 4 are summarized in Table 1 below.

TABLE 1

| Section | Methylenechloride (A) (ml) | Isopropanol (B) (ml) | Water (C) (ml) | Solvent ratio (A:B:C) | Yield (%) | Z/E isomer ratio |
| --- | --- | --- | --- | --- | --- | --- |
| Example 3 | 150 | 150 | 50 | 11:3:1 | 83 | 8.9/1 |
| Example 2 | 200 | 200 | 50 | 12:4:1 | 86 | 10.1/1 |
| Example 4 | 300 | 300 | 50 | 14:6:1 | 85 | 9.1/1 |

As presented in Table 1, when a mixed solvent including methylenechloride, isopropanol, and water was used according to a solvent ratio as defined in the present invention, 3-propenyl cephem compounds of formula 1 were stereospecifically prepared in high yield. In particular, when the volume ratio of methylenechloride, isopropanol, and water was 12:4:1, the most excellent results were provided in terms of yield and purity.

EXAMPLE 5

Preparation of 7-amino-3-[propen-1-yl]-3-cephem-4-carboxylic acid 22.8 g of phosphorus pentachloride, 150 ml of methylenechloride, and 8.88 ml of pyridine were placed in a 20° C. reactor and stirred for 30 minutes. 30 g (62.6 mmol) of the 7-phenylacetamido-3-[propen-1-yl]-3-cephem-4-carboxylic acid p-methoxybenzyl ester prepared in Example 2 was dropwise added thereto and stirred for 2 hours. The reaction mixture was cooled to −10° C. and was stirred for 2 hours after addition of 30 ml of 1,2-propanediol and then for 2 hours after addition of 120 ml of cresol. 200 ml of distilled water was dropwise added thereto and stirred for 1 hour. After phase separation, an aqueous layer was sent to a crystallization bath, and an organic layer was extracted with 300 ml of 2N HCl and then the extract was sent to the crystallization bath. 200 ml of a 30% sodium hydroxide solution was dropwise added to the crystallization bath for crystallization and then cooled to 0° C. An obtained solid was filtered and dried in vacuum to give 12 g (50 mmol, yield 80%, Z/E=10.1/1) of the titled compound as a beige solid.

H-NMR($\delta$, $D_2O$+$NaHCO_3$): 1.69 and 1.88(3H, each, d, 6.0 Hz, —CH=CH—$CH_3$), 3.38 and 3.72(2H, Abq, 17 Hz, H-2), 5.18(1H, d, 5.0 Hz, H-6), 5.51(1H, d, H-7), 5.8(1H, m, —CH=$CH$—$CH_3$), 6.06(1H, d, 11 Hz, —$CH$=CH—$CH_3$)

EXAMPLE 6

Preparation of 7-[2-amino-2-(4-hydroxyphenyl)acetamido]-3-[propen-1-yl]-3-cephem-4-carboxylic acid (cefprozil)

The reaction solution obtained in step A of Example 1 was cooled to −40° C. and a solution obtained by dissolving 6.88 g (0.029 mol) of the 7-amino-3-[propen-1-yl]-3-cephem-4-carboxylic acid prepared in Example 5 in 40 ml of methylenechloride, 10 ml of water, and 6.5 g of triethylamine was gradually dropwise added thereto for 1 hour.

Then, the reaction mixture was incubated at the same temperature for 2 hours and cooled to 0° C. to obtain an insoluble solid. The insoluble solid was filtered. A filtrate was sent to a reactor and then stirred for 1 hour after addition of 20 ml of 6N HCl. The reaction solution was adjusted to pH of 3.2 by addition of 10% NaOH, stirred at 0° C. for 2 hours, and filtered to give 9.6 g (83%) of the titled compound as a white solid.

H-NMR($\delta$, $D_2O$-$d_2$): 1.65(3H, d, 8.6 Hz, —CH=CH $CH_3$cis)), 1.81(0.21H, d, 8.6 Hz, —CH=CH$CH_3$(trans)), 3.22(1H, d, 18 Hz, 2-H), 3.55(1H, d. 18 Hz, 2-H), 5.15(1H, d, 4.6 Hz, 6-H), 5.66(1H, d, 4.6 Hz, 7-H), 5.75(1H, m, vinyl-H), 5.96(1H, m, vinyl-H), 6.91(2H, d, 8.0 Hz, phenyl-H), 7.38 (2H, d, 8.0 Hz, phenyl-H)

EXAMPLE 7

Preparation of 7-[2-amino-2-(4-hydroxyphenyl)acetamido]-3-[propen-1-yl]-3-cephem-4-carboxylic acid (cefprozil)

A reaction solution obtained in the same manner as in step A of Example 1 except that 100 ml of dimethylacetamide was used instead of methylenechloride was cooled to −40° C. and then a solution obtained by dissolving 6.88 g (0.029 mol) of the 7-amino-3-[propen-1-yl]-3-cephem-4-carboxylic acid prepared in Example 5 in 50 ml of dimethylacetamide, 10 ml of water, and 6.5 g of triethylamine was gradually dropwise added thereto for 1 hour.

Then, the reaction mixture was incubated at the same temperature for 2 hours and cooled to 0° C. to obtain an insoluble solid. The insoluble solid was filtered. A filtrate was sent to a reactor and then stirred for 1 hour after addition of 20 ml of 6N HCl. The reaction solution was adjusted to pH of 3.2 by addition of 10% NaOH, stirred at 0° C. for 2 hours, and filtered to give 9.4 g (82%) of the titled compound as a white solid.

EXAMPLE 8

Preparation of 7-[2-amino-2-(4-hydroxyphenyl)acetamido]-3-thiomethyl-[1,2,3-triazole-5-yl]-3-cephem-4-carboxylic acid (cefatrizine)

The reaction solution obtained in step A of Example 1 was cooled to −40° C. and a solution obtained by dissolving 6.88 g (0.029 mol) of 7-amino-3-[1,2,3-triazole-5-yl]-3-cephem-4-carboxylic acid in 50 ml of methylenechloride, 10 ml of water, and 6.5 g of triethylamine was gradually dropwise added thereto for 1 hour.

Then, the reaction mixture was incubated at the same temperature for 2 hours and cooled to 0° C. to obtain an insoluble solid. The insoluble solid was filtered. A filtrate was sent to a reactor and then stirred for 1 hour after addition of 20 ml of 6N HCl. The reaction solution was adjusted to pH of 3.5 by addition of 10% NaOH, stirred at 0° C. for 2 hours, and filtered to give 10.7 g (80%) of the titled compound as a white solid.

H-NMR($\delta$, $D_2O$-$d_2$): 3.22(1H, d, 18 Hz, 2-H), 3.55(1H, d. 18 Hz, 2-H), 3.60(2H, m, —$\underline{CH_2}$—S—), 5.15(1H, d, 4.6 Hz, 6-H), 5.66(1H, d, 4.6 Hz, 7-$\underline{H}$), 6.91(2H, d, 8.0 Hz, phenyl-H), 7.38(2H, d, 8.0 Hz, phenyl-H), 7.93(1H, d, 8.2 Hz, —$\underline{CH}$—NH—)

EXAMPLE 9

Preparation of 7-[2-amino-2-(4-hydroxyphenyl)acetamido]-3-methyl-3-cephem-4-carboxylic acid (cefadroxil)

The reaction solution obtained in step A of Example 1 was cooled to −40° C. and a solution obtained by dissolving 6.21 g (0.029 mol) of 7-amino-3-methyl-3-cephem-4-carboxylic acid in 40 ml of methylenechloride, 10 ml of water, and 6.5 g of triethylamine was gradually dropwise added thereto for 1 hour.

Then, the reaction mixture was incubated at the same temperature for 2 hours and cooled to 0° C. to obtain an insoluble solid. The insoluble solid was filtered. A filtrate was sent to a reactor and then stirred for 1 hour after addition of 20 ml of 6N HCl. The reaction solution was adjusted to pH of 3.2 by addition of 10% NaOH, stirred at 0° C. for 2 hours, and filtered to give 9.1 g (83%) of the titled compound as a white solid.

H-NMR($\delta$, $D_2O$-$d_2$): 1.79(3H, d, 8.6 Hz, —$CH_3$), 3.22 (1H, d, 18 Hz, 2-H), 3.55(1H, d. 18 Hz, 2-H), 5.15(1H, d, 4.6 Hz, 6-H), 5.66(1H, d, 4.6 Hz, 7-H), 6.91(2H, d, 8.0 Hz, phenyl-H), 7.38(2H, d, 8.0 Hz, phenyl-H)

According to the present invention, a cephalosphorin antibiotic can be prepared in high yield and purity using a 4-hydroxyphenylglycine derivative without further separation and purification. In particular, a cephalosporin antibiotic, including cefprozil or its salt, can be prepared in high yield and purity by reacting a 4-hydroxyphenylglycine derivative with a 3-(Z)-propenyl cephem derivative stereospecifically synthesized.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A process for preparing a compound represented by the following formula 1 or its salt, which comprises reacting a compound represented by the following formula 2 with a compound represented by the following formula 3 in the presence of a base:

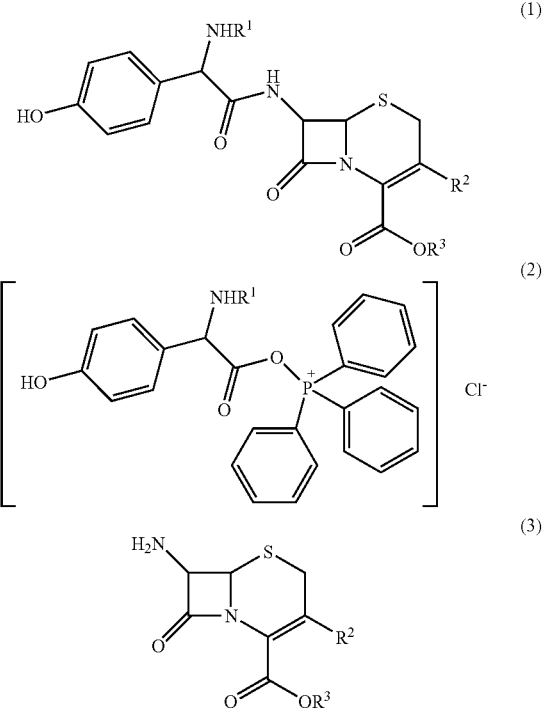

wherein $R^1$ is a hydrogen or an amino protecting group, $R^2$ is methyl, propen-1-yl, or 1H-1,2,3-triazole-4-yl-thiomethyl, and $R^3$ is a hydrogen or a carboxyl protecting group.

2. The process of claim 1, wherein the compound of the formula 2 is in anhydrous form.

3. The process of claim 1, wherein the equivalent ratio of the compound of formula 2 to the compound formula 3 is 1.1-1.5 to 1.

4. The process of claim 1, wherein the compound of the formula 2 reacts with the compound of the formula 3 in a mixed solvent of water with an organic solvent selected from the group consisting of dimethylsulfoxide, dimethylformamide, dimethylacetamide, 1,4-dioxane, acetonitrile, dichloromethane, and a mixture thereof.

5. The process of claim 4, wherein in the mixed solvent, water is used in an amount of 0.05 to 0.3 parts by weight, based on 1 part by weight of the organic solvent.

6. The process of claim 1, wherein the base is selected from the group consisting of N-methylmorpholine, triethylamine, diethylamine, n-tributylamine, N,N-dimethylaniline, and pyridine.

7. A compound represented by the following formula 2:

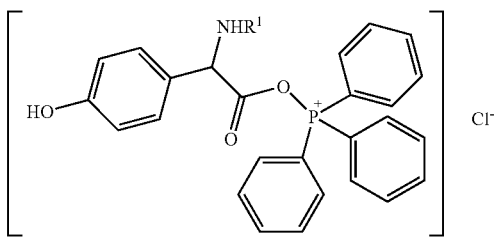
(2)

wherein $R^1$ is a hydrogen or an amino protecting group.

8. The compound of claim 7, which is in anhydrous form.

9. A process for preparing a compound represented by the following formula 2, which comprises reacting a compound represented by the following formula 4 with dichlorotriphenylphosphorane in the presence of a base:

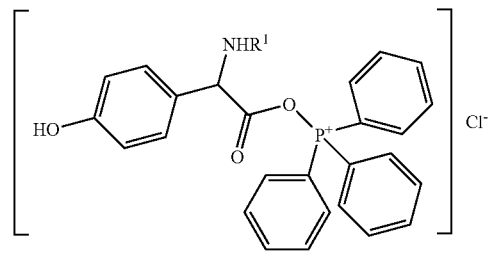
(2)

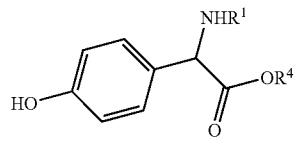
(4)

wherein $R^1$ is a hydrogen or an amino protecting group, and $R^4$ is hydrogen, sodium, or potassium.

10. The process of claim 9, wherein the equivalent ratio of the compound of the formula 4 to dichlorotriphenylphosphorane is 1 to 1.1-1.5.

11. The process of claim 9, wherein the compound of the formula 4 reacts with dichlorotriphenylphosphorane in an organic solvent selected from the group consisting of dichloromethane, acetonitrile, tetrahydrofuran, and a mixture thereof.

12. The process of claim 9, wherein the base is selected from the group consisting of triethylamine, diethylamine, n-tributylamine, N,N-dimethylaniline, and pyridine.

13. The process of claim 9, wherein dichlorotriphenylphosphorane is obtained by reaction between triphenylphosphine and hexachloroethane.

14. The process of claim 13, wherein the reaction of triphenylphosphine and hexachloroethane and the reaction of the compound of the formula 4 and dichlorotriphenylphosphorane in the presence of a base are performed by one-pot reaction.

* * * * *